United States Patent [19]

Mueller et al.

[11] 4,101,557
[45] * Jul. 18, 1978

[54] SELECTIVE SYNTHESIS OF 2-HALOALKANETHIOLS AND EPISULFIDES THEREFROM

[75] Inventors: Wolfgang H. Mueller, Neuallschwil, Switzerland; Alexis A. Oswald, Mountainside, N.J.; Peter J. Kozak, Sarnia, Canada

[73] Assignee: Exxon Research & Engineering Co., Linden, N.J.

[ * ] Notice: The portion of the term of this patent subsequent to Mar. 4, 1993, has been disclaimed.

[21] Appl. No.: 32,457

[22] Filed: Apr. 27, 1970

Related U.S. Application Data

[63] Continuation-in-part of Ser. No. 581,441, Sep. 23, 1966, Pat. No. 3,994,889.

[51] Int. Cl.$^2$ ............................................. C07D 331/02
[52] U.S. Cl. ............................ 260/327 E; 260/609 B; 204/158 R; 204/158 HE
[58] Field of Search ...................... 260/327 E, 609 B; 204/158 R, 158 HE

[56] References Cited

U.S. PATENT DOCUMENTS

| | | | |
|---|---|---|---|
| 2,183,860 | 12/1939 | Coltof | 260/327 |
| 2,398,480 | 4/1946 | Vaughan | 204/158 |
| 2,551,813 | 5/1951 | Pinkney | 260/609 |
| 3,045,053 | 7/1962 | Ford | 260/609 |
| 3,412,001 | 11/1968 | Edwards | 204/162 |

FOREIGN PATENT DOCUMENTS

| | | | |
|---|---|---|---|
| 593,722 | 3/1960 | Canada | 204/158 |
| 1,173,157 | 12/1969 | United Kingdom | 260/327 |

*Primary Examiner*—Henry R. Jiles
*Assistant Examiner*—CMS Jaisle
*Attorney, Agent, or Firm*—J. E. Luecke; F. Santoro

[57] ABSTRACT

Haloalkanethiols are synthesized through the free radical liquid phase reaction of halogenated olefins with an excess of hydrogen sulfide. High product yields to the desired haloalkanethiol products are secured when a 3 to 20 fold molar excess of hydrogen sulfide to halogenated olefin is used. Desirably, the synthesis is carried out to a conversion level not exceeding 90%. The haloalkanethiol products can be subsequently dehydrohalogenated to the corresponding episulfide products by reacting the haloalkanethiol product with a substantially equal molar amount of anhydrous ammonia.

10 Claims, No Drawings

SELECTIVE SYNTHESIS OF 2-HALOALKANETHIOLS AND EPISULFIDES THEREFROM

CROSS-REFERENCE TO RELATED APPLICATION

This application is a continuation-in-part of Ser. No. 581,441, filed Sept. 23, 1966 now U.S. Pat. No. 3,994,889 in the names of Wolfgang H. Mueller, Alexis A. Oswald and Peter J. Kozak.

BACKGROUND OF THE INVENTION

1. Field of the Invention

This invention relates to methods for the formation of halogenated aliphatic thiols and episulfides. More particularly, this invention relates to techniques for producing 2-haloalkanethiols by reacting halogenated olefins with excess hydrogen sulfide and to subsequently converting the 2-haloalkanethiols to the corresponding monomeric episulfide with equimolar amounts of anhydrous ammonia. As such the invention is useful for the preparation of 2-haloalkanethiol pesticides and intermediates, and episulfide monomers.

2. Description of the Prior Art

Episulfides are reactive, desirable monomers. They are useful for the preparation of a variety of polymers ranging from engineering plastics to solvent resistant elastomers. Several synthetic approaches are known for the preparation of episulfides. Nevertheless, no episulfide is commercially manufactured because all the known processes are characterized by either low yield performance or involve expensive intermediates. The present invention unexpectedly improves the yields of two known reactions by using specific, critical process conditions. The two reactions related to the present invention are discussed below:

The first reaction, i.e., the free radical type addition of hydrogen sulfide to vinylic halides, has been known since 1946. However, there is no known process for carrying it out so as to obtain the corresponding β-haloalkanethiol monoadducts. For example, the addition of $H_2S$ to vinyl chloride $$CH_2=CHCl \xrightarrow{H_2S} HSCH_2CH_2Cl \xrightarrow{CH_2=CHCl} ClCH_2CH_2SCH_2CH_2Cl$$

was described in U.S. Pat. No. 2,398,480. However the patentee failed to secure high selectivity levels for the formation of the 2-chloroethanethiol monoadduct. The major portion of the product was the diadduct, i.e. di-2-chloroethyl sulfide, commonly known as mustard gas.

In general, an excess of $H_2S$ might be employed to increase the selectivity of $H_2S$/olefin additions to monoadduct products. In the case of vinylic halides, however, the excess of hydrogen sulfide is expected to enter secondary reactions with the 2-haloalkanethiol monoadducts. 2-Haloalkanethiols are generally known to be unstable and highly reactive. For example, C. C. Price and P. F. Kirk describe in the Journal of the American Chemical Society, in volume 75, page 2400 (1953), that 3-chloro-2-butanethiol releases hydrogen chloride on distillation. In the presence of hydrogen chloride an equilibrium is established between β-haloalkanethiols and the corresponding episulfides. This equilibrium is discussed by N. V. Schwartz in the Journal of Organic Chemistry, volume 3, pages 2895 to 2902 (1968). In the case of 2-chloropropanethiol the following reactions are involved:

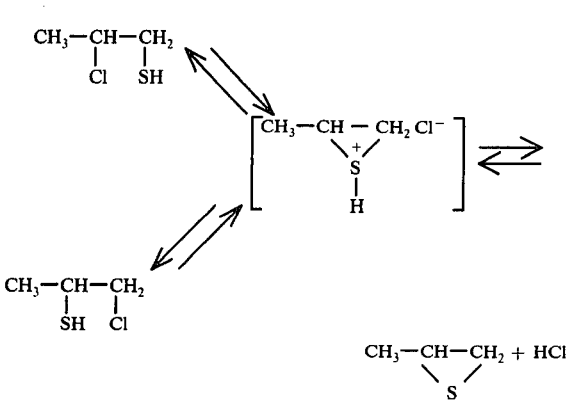

The episulfide equilibrium product is known to react with hydrogen sulfide. For example, E. M. Meade and F. N. Woodward describe in the Journal of the Chemical Society, pages 1894 and 1895 (1948) that ethylene episulfide reacts with $H_2S$ to yield ethanedithiol. It is well known in physical chemistry that the consequence of the elimination one product of an equilibrium is the shift of the equilibrium. In the case of the chloroethanethiol-ethylene episulfide equilibrium, the reaction of the episulfide with hydrogen sulfide should consequently lead to the conversion of the 2-chloroalkanethiol to ethanedithiol:

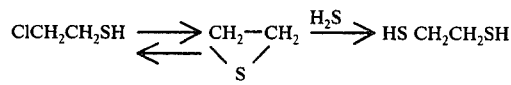

In view of the above reaction, an excess of hydrogen sulfide would be expected to have an adverse effect on the yield of 2-haloalkanethiols from vinylic halides. Indeed, to date, no such high yield synthesis is known.

In accordance with the present invention, it has been surprisingly discovered that 2-haloalkanethiols can be synthesized from vinylic halides in high yields by using at least a 3:1 molar excess of the hydrogen sulfide reactant and carrying the addition to a conversion of less than 90% of the vinylic halide reactant.

The dehydrohalogenation of 2-haloalkanethiols by certain bases to yield episulfides is known. The reaction was described in 1939 by W. Coltof in U.S. Pat. No. 2,183,860. According to Coltof the dehydrohalogenation is carried out under slightly alkaline conditions. In the case of weak bases, an excess of the base in water is used.

Coltof states that inorganic nitrogen bases are suitable dehydrohalogenation agents. Such bases would normally include anhydrous ammonia. However, ammonia is known to polymerize the episulfide product of dehydrohalogenation. This polymerization is described by M. Ohta, A. Kondo and R. Ohi in the Nippon Kagaku Zasshi, volume 75, pages 985 and 986 (1954) (see Chemical Abstracts, Vol. 51, page 14668$^e$, year 1957). Such a polymerization would probably involve the N-H bonds of ammonia as indicated by the reaction scheme,

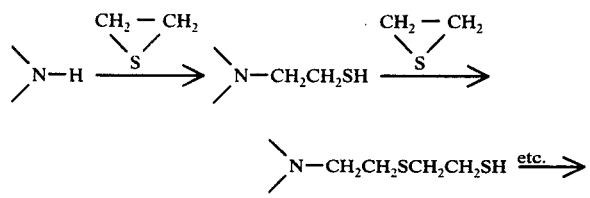

discussed on page 164 of volume IX of Houben-Weyl's Methoden der Organischem Chemie, which was published by Verlag Chemie in Weinheim, W. Germany in 1965.

Consequently, in view of the overall information from the prior art, an episulfide sulfide synthesis using ammonia as a reactant does not seem feasible. It has now been found surprisingly that if an equimolar amount of anhydrous ammonia is used, instead of an excess of the aqueous reagent, a high yield synthesis of episulfides from 2-haloalkanethiols becomes feasible.

The overall concept of the present invention embraces the combination of the above processes plus three known reactions in a cyclic process sequence which converts olefins to episulfide monomers with the net consumption of hydrogen sulfide and oxygen.

SUMMARY OF THE INVENTION

The present invention provides a highly selective technique for the formation of 2-haloalkanethiol materials and the corresponding episulfides therefrom. In step one 2-haloalkanethiol materials are secured in substantial yield and at high selectivities by reacting halogenated olefins, in particular vinylic halides, with at least a 3:1 molar excess of hydrogen sulfide in the presence of a free radical initiator. The reaction is carried out to a maximum conversion of 90% of the olefin. Preferably, the olefin conversion is less than 60%. In the second step, the 2-haloalkanethiols are converted to the corresponding episulfides by dehydrohalogenation with ammonia. Surprisingly, essentially quantitative episulfide yields are secured when substantially equimolar amounts of anhydrous ammonia are employed.

The starting materials for making the 2-haloalkanethiols are vinylic halides, i.e., halogen substituted olefins. The olefin may have terminal and/or internal type double bonds. In the case of a diolefin, the halo-substituent may be present on either one or on both olefinic groups. In general, the desired reaction is shown by the following reaction scheme:

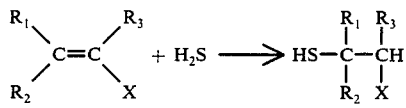

wherein $R_1$, $R_2$ and $R_3$ can each be hydrogen and $C_1$ to $C_{20}$ non-substituted or monosubstituted monovalent hydrocarbon radicals preferably selected from monovalent $C_1$ to $C_{20}$, preferably $C_1$ to $C_{12}$, alkyl; $C_7$ to $C_{20}$ aralkyl, preferably phenyl-alkyl, $C_6$ to $C_{14}$ aryl, preferably phenyl, $C_2$ to $C_{20}$, preferably $C_2$ to $C_{12}$ alkenyl, $C_1$ to $C_{16}$, preferably $C_1$ to $C_{12}$, chloroalkyl hydroxyalkyl, mercaptoalkyl, halogenated alkoxyalkyl and alkylthioalkyl radicals. Most preferably $R_1$, $R_2$ and $R_3$ are hydrogen and methyl radicals and X can be a fluorine, chlorine or bromine atom. Chlorine and bromine, particularly chlorine, are the preferred halogen species.

It is preferred that at least one of the R groups of the vinylic halide reactants be a hydrogen atom. It is more preferable that two of the R groups be hydrogen atoms. Furthermore, from the viewpoint of high reactivity towards the hydrogen sulfide, it is desirable that $R_1$ and $R_2$ should be hydrogen atoms. The free radical type addition to vinylic halides occurs in an anti-Markovnikov manner to yield the desired β-haloalkanethiols. For example, 2-chloroalkenes react as it is shown by the following equation:

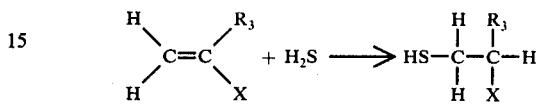

When alkyl monosubstituted vinylic halides are reacted with hydrogen sulfide, a much faster reaction takes place if the halogen and the alkyl substituents are on the same carbon atom. For example it has been found that when a mixture of 1-chloropropene and 2-chloropropene is treated with a large excess of hydrogen sulfide, the addition of $H_2S$ takes place to 2-chloropropene in preference to 1-chloropropene. Thus, the process of this invention can also be used to obtain pure 1-chloropropene from a mixture of 1- and 2-chloropropenes.

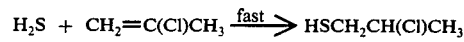

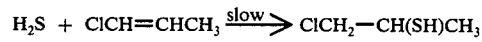

Representative examples of useful vinylic halide reactants are vinyl bromide, 2-propenyl fluoride, 2-butenyl iodide, 1-dodecenyl chloride, 1-nonadecenyl chloride, vinyl chloride, 2-hexadecenyl chloride, cyclohexenyl chloride, cyclododecadienyl chloride, cyclopentadienyl chloride, styryl chloride, phenyl dodecenyl chloride, chloropropenyl chloride, hydroxybutenyl chloride, mercaptopropenyl chloride, chloropropyloxybutenyl chloride.

In the second step of the present process the 2-haloalkanethiol intermediate products are reacted with equimolar amounts of anhydrous ammonia to yield the corresponding episulfides as final products according to the following equation:

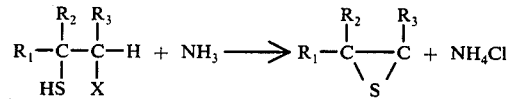

wherein $R_1$, $R_2$, $R_3$ and X are as previously described.

Representative examples of useful 2-haloalkanethiol reactants are: chloroethanethiol, chloropropanethiol, chlorobutanethiol, chlorononadecanethiol, chlorophenylethanethiol, chloroethoxybutanethiol, chlorocyclohexenethiol, bromobutanethiol.

The addition of hydrogen sulfide to the vinylic halide is carried out using an excess of $H_2S$ in the presence of free radical type initiators in the liquid phase. To achieve the high selectivity a 3 to 20 fold preferably a 7 to 14 fold molar excess of $H_2S$ is required.

The free radical initiators of the reaction include chemical products and radiation. Examples of effective chemical initiators are azo compounds, such as azo-bisisobutyronitrile, and peroxides such as dialkyl peroxides, e.g., bis-t-butyl peroxide, aliphatic hydroperoxides, e.g., t-butyl hydroperoxide and cumene hydroperoxide, and acyl peroxides, e.g., benzoyl peroxide. Radiation initiators include ultraviolet light and gamma-rays. The amount of chemical initiator employed may vary from 0.1 to 5 mole percent of the olefin reactant. The rate of radiation initiation is dependent on its intensity and wavelength. The effectiveness of ultraviolet radiation can be improved by photosensitizers. Combinations of radiation and chemical initiators can be used to advantage.

The reaction is carried out in the liquid phase at temperatures in the range of about $-100°$ to $+100°$ C., preferably $-50°$ to $50°$ C., more preferably at $-20°$ to $+30°$ C. The reaction is largely independent of the pressures used. However, to keep the hydrogen sulfide in the liquid phase superatmospheric pressures are often necessary. Normally, pressures ranging from 1 to 100 atmospheres are used.

The reaction temperature is selected so as to avoid subsequent product reactions. Unsubstituted 2-haloethanethiols are highly reactive and as such should be produced below $30°$. With an increasing number of alkyl substituents, product stability is increased and higher reaction temperatures can be applied. Higher temperatures may be necessary for chemically initiated reactions wherein radical generation may require heating.

The reaction does not require the use of solvents. However, in some cases, solvents can be advantageously used to avoid reactant and product precipitation or to reduce the necessary pressure. Suitable inert solvents include aliphatic and aromatic hydrocarbons, such as cyclohexane and toluene, ethers and thioethers such as tetrahydrofuran and diethyl sulfide.

The reaction is run to a maximum of 90% conversion of the vinylic halide. However, conversion levels below 60% are preferred. Too high conversions result in secondary reactions and decreased utilization of the initiators. The reaction times necessary for desirable conversions depend on the rate of initiation. For batch type operations, they may range from 25 minutes to 48 hours, preferably from 2 hours to 12 hours. In a continuous operation higher initiation rates are coupled with shorter reaction times in the order of 5 minutes to 60 minutes. In a large scale industrial application of this process a continuous low conversion operation with reactant recycle is assumed. For example, gaseous vinyl chloride and hydrogen sulfide are pumped through compressors in the proper ratios to be mixed, liquefied under pressure and converted in reaction coils under the effect of gamma irradiation. In the subsequent decompression stage, the liquid 2-chloroethanethiol and byproducts are drained and the gaseous unconverted starting materials are recycled.

The dehydrohalogenation of the 2-haloalkanethiol by ammonia is carried out using substantially equimolar amounts of the anhydrous reactants in the liquid phase.

To achieve high yields excess ammonia and the presence of water should be avoided. The ammonia is best introduced slowly into the effectively stirred and cooled 2-haloalkanethiol. This manner of addition will avoid the temporary formation of basic locations. In contrast to the Coltof process, it assures that the whole process will take place in the absence of significant amounts of a free base. At the completion of the reaction essentially all the chlorine and the nitrogen will be in the form of ammonium chloride. The latter, when dissolved to give a 5 percent aqueous solution, will show a pH of 5. This acidic reaction is contrasted with the neutral or slightly basic conditions of Coltof.

The episulfide formation reaction is carried out in the liquid phase at temperatures in the range of about $-50°$ to $+50°$, preferably $-10°$ to $30°$. The control of temperature is especially critical in the case of the reactive unsubstituted 2-haloalkanethiols which yield relatively unstable, highly reactive ethylene sulfide. Although one of the reactants is a gas, pressures approximating atmospheric conditions can be used. The ammonia is usually slowly introduced into the stirred reactor at a pressure of 0.5 to 3 atmospheres.

The reaction is usually carried out in the absence of solvents; however, the use of inert solvents may be advantageous. It is preferred to use solvents which do not dissolve the byproduct ammonium chloride. The solvents used for the $H_2S$-addition step are suitable here as well.

The episulfide formation reaction is run to a minimum 90% conversion of the 2-haloalkanethiol. The dehydrohalogenation by anhydrous ammonia is very rapid. Nevertheless, due to the exothermicity of the reaction the reaction is prolonged by introducing the ammonia slowly. Depending on the size of the 2-haloalkanethiol batch to be converted, the time required for conversion may vary from 30 minutes to 12 hours.

The two selective reaction steps of the present invention provide an attractive route for the conversion of vinylic halides, preferably vinylic chloride, to episulfides. Some of the vinylic chlorides, such as vinyl chloride, are commercially available in high purity. Other vinylic chlorides can be made by inexpensive processes as mixtures of structural isomers. For example, mixtures of 1- and 2-chloroalkenes can be readily derived from 1-alkenes via chlorination followed by dehydrochlorination. Both chloroalkenes can be converted to the same episulfide by the present two step process. Furthermore, the ammonium chloride by-product of the process can be used for the production of ammonia and chlorine by the procedure set forth in French Pat. No. 1,385,447.

Our invention combines in a broad concept the above reaction to provide a cyclic process in which olefins, preferably 1-alkenes, are converted to the corresponding episulfides with the net consumption of only hydrogen sulfide and oxygen. This cyclic process is illustrated with 2-chloroalkanethiol intermediates by the reaction scheme set forth below.

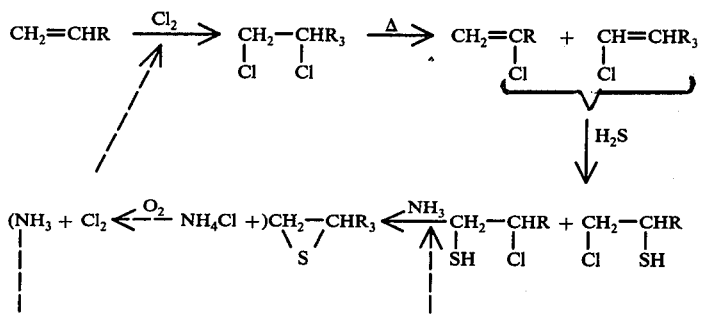

wherein R is hydrogen, a $C_1$ to $C_{20}$ preferably $C_1$ to $C_3$ alkyl.

DESCRIPTION OF THE PREFERRED EMBODIMENTS

EXAMPLE 1

Vinyl chloride (20.2 grams, 0.32 mole) and 99.8 grams (2.93 moles) of $H_2S$ were condensed in a quartz tube equipped with a magnetic stirring bar. The sealed tube was irradiated with a high pressure mercury arc (70 W Hanau immersion lamp) for 15 hours at 17° C. After release of the excess $H_2S$, 31.1 grams of a yellow liquid was obtained. Gas liquid chromatography of the product mixture indicated 92 peak area percent of 2-chloroethanethiol and 8 peak area percent of $\beta,\beta'$-dichlorodiethyl sulfide. Distillation of the products afforded 23 grams (74% yield) of 2-chloroethanethiol, b.p. 62° to 63°/118 mm, and 5.6 grams (about 12% yield) of residual $\beta,\beta'$-dichlorodiethyl sulfide. The products were identified by nuclear magnetic resonance spectroscopy. The amount of total products formed indicates a vinyl chloride conversion of about 85%.

EXAMPLE 2

Vinyl chloride (12.5 grams, 0.2 mole) and hydrogen sulfide (68 grams, 2 moles) were condensed in a Pyrex tube equipped with a magnetic stirring bar. The sealed tube was gamma irradiated at about 30° C. under autogeneous pressure at ambient temperature for one hour. A $10^6$ gamma/hour $Co^{60}$ source was placed at a distance of 7 cm from the reactor. After removal of the unreacted starting materials, 10 grams (52% yield) of the desired 2-chloroethanethiol was attained as a liquid residue. Its purity was 91.5% as determined by g.l.c. and n.m.r. techniques.

Approximately 8% of the mustard gas was formed as byproduct. Since the nonvolatiles represent the total amount of products, the conversion in this experiment was about 60%.

EXAMPLE 3

In a series of experiments carried out under the conditions described in Example 2, the effect of increasing excess of hydrogen sulfide reactant and of increasing conversion of the vinyl chloride reactant was studied. In the same series of experiments, the effectiveness of gamma irradiation as measured by the so-called G values, that is, the number of molecules formed per 100 electrol volts, was also determined under the various experimental conditions. The data are shown in Table I.

TABLE I

| Irradiation Time (hrs.) | $CH_2$=CHCl:$H_2S$ Molar Ratio | Conversion % | Selectivity Mole % | G-Value |
|---|---|---|---|---|
| 0.25 | 1 : 3 | 27.0 | 90 | 7.93 × $10^3$ |
| 0.5 | 1 : 3 | 66.0 | 82.1 | 9.94 × $10^3$ |
| 1 | 1 : 3 | 67.9 | 82.3 | 5.79 × $10^3$ |
| 0.5 | 1 : 10 | 27.8 | 91.5 | 2.48 × $10^3$ |
| 1 | 1 : 10 | 51.9 | 91.5 | 2.58 × $10^3$ |
| 5 | 1 : 10 | 61.2 | 93 | 0.73 × $10^3$ |
| 10 | 1 : 10 | 67.4 | 76.3 | 0.27 × $10^3$ |

The results indicate that with increasing conversion a large decrease in selectivity to 2-chloroethanethiol occurs. At a low conversion level, high selectivities are obtained starting with a threefold molar excess of hydrogen sulfide and up. An increasing hydrogen sulfide excess, however, tends to reduce the effectiveness of the initiation, especially at higher conversions, as shown by the decreasing G values.

EXAMPLE 4

A 4 to 1 mixture of 1- and 2-chloropropene (26 grams, 0.6 mole) and 209 grams of $H_2S$ was irradiated with ultraviolet light for 20 hours in a magnetically stirred and sealed quartz tube. The irradiation was carried out in a temperature controlled water bath at 17° with a 70 W medium pressure mercury arc Hanau ultraviolet lamp. After release of the excess $H_2S$, 15.8 grams of unreacted starting material was distilled off. G.l.c. analysis showed it to be pure 1-chloropropene. The residue 29.4 grams (45% yield) showed ca. 95% of the isomeric $\beta$-chlorothiols and 5% of $\beta,\beta'$-dichlorodipropyl sulfide on analysis. The isomeric mixture of mercaptans distilled at 124° to 125°.

EXAMPLE 5

A mixture of 1-chloropropene and 2-chloropropene was reacted with a 10-fold excess of hydrogen sulfide. Reaction conditions were identical to those described in Example 2. However, prolonged gamma irradiation up to ten hours was employed. The corresponding isomeric $\beta$-chloropropyl mercaptans were formed in 94% selectivity at the 44% conversion level.

EXAMPLE 6

To 9.65 grams (0.1 mole) of 2-chloroethyl mercaptan, 1.71 grams of ammonia was slowly introduced under stirring. The reaction temperature was kept at −20° C. After the addition was completed, the ethylene episulfide was removed from the $NH_4Cl$ at room temperature. The product, 5.1 grams, was 99% pure on g.l.c. analysis and represents 90% yield at 95% conversion.

EXAMPLE 7

Ammonia (0.85 gram, 0.05 mole) was condensed into a Pyrex tube at −80°, then 5.5 grams (0.05 mole) of an isomeric mixture of 1-chloro-2-mercapto-propane and 2-chloro-1-mercaptopropane (containing ca. 5% of 2,2'-dichlorodipropyl sulfide) was added and the tube sealed. After one hour at 0° the tube was slowly warmed up to room temperature and the propylene sulfide distilled off at 0.2 mm ambient temperature. In a dry-ice cooled trap, 3.1 grams (84% yield) of propylene sulfide was collected. The product was identified by comparison of g.l.c. and n.m.r. data with those of an authentic sample.

The distillation residue contained the sulfide present in the starting material and $NH_4Cl$.

EXAMPLE 8

The 2-haloalkanethiols synthesized in Examples 1, 2 and 4 and the episulfide obtained in Example 7 were tested as nematocides. The nematocidal tests were carried out by the so-called modified method of the Wisconsin Alumni Research Foundation using tomato plants potted in soil infested with an unknown strain of parasitic root knot nematode. Evaluation of the effectiveness of the compounds was made on the basis of the signs of nematode activity. Two groups of plants were used during the test. One group, the Control, was not treated; a second group, the Test group, was treated by applying the thiols and episulfides of the invention at a rate of twenty pounds of compound per acre. After about six weeks the plants were pulled up, and the number of knots on the roots were counted. The difference in the number of knots formed in the Control and Test groups expressed as a percent of the number of knots formed in the Control group indicates the effectiveness of the particular compound for use in nematode control. The results of these tests are shown in Table II.

TABLE II

| Compound | Control of Nematodes % Reduction |
|---|---|
| $Cl-CH_2-CH_2-SH$ | 100 |
| $Cl-CH_2-CH(SH)-CH_3$ and $HS-CH_2-CH(Cl)-CH_3$ | 20 |
| $CH_2-CH-CH_3$ with S bridge | 17 |

The data show these compounds, especially the vinyl chloride adduct, control nematodes at a low application rate.

What is claimed is:

1. A process for preparing monomeric episulfides which comprises reacting a haloalkanethiol of the general formula

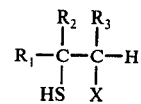

wherein $R_1$, $R_2$ and $R_3$ are hydrogen and $C_1$ to $C_{20}$ nonsubstituted or monosubstituted monovalent hydrocarbon radicals and X is halogen, with a substantially equal molar amount of anhydrous ammonia at a temperature varying from about −50° to +50° and at a pressure of 0.5 to 3 atmospheres.

2. The process of claim 1 wherein X is a chlorine atom.

3. The process of claim 1 wherein said haloalkanethiol is selected from the group consisting of 2-chloroethanethiol and its $C_1$ to $C_{20}$ alkyl monosubstituted derivatives.

4. The process of claim 1 wherein said haloalkanethiol is 2-chloropropanethiol and 1-chloro-2-propanethiol.

5. The process of claim 1 wherein said haloalkanethiol is 2-chloroethanethiol.

6. A process for the conversion of vinylic halides to episulfides comprising:
    (a) reacting a vinylic halide with a 3 to 20 fold molar excess of hydrogen sulfide in the liquid phase in the presence of a free radical initiator for a time sufficient to secure up to a 90% conversion of said vinylic halide and recovering the corresponding 2-haloalkanethiol as the major product, and
    (b) reacting the said 2-haloalkanethiol with substantially equimolar amounts of anhydrous ammonia to obtain monomeric episulfide.

7. The process of claim 6 wherein said vinylic halide is a vinylic chloride.

8. The process of claim 6 wherein the vinylic halide is a $C_2$ to $C_{20}$ 1-alkenyl chloride.

9. The process for preparing monomeric ethylene episulfide which comprises reacting 2-chloroethanethiol with a substantially equal molar amount of anhydrous ammonia at a temperature varying from about −10° plus 30° C at a pressure of 0.5 to 3 atmospheres and removing the resulting ethylene sulfide product from the solid ammonium chloride by-product precipitate.

10. The process for preparing monomeric propylene episulfide which comprises reacting a mixture of 1-chloropropanethiol and 2-chloropropanethiol with a substantially equal molar amount of anhydrous ammonia at a temperature varying from −50° to +50° C. at a pressure of 0.5 to 3 atmospheres and removing the resulting propylene sulfide product from the solid ammonium chloride by-product precipitate.

* * * * *